US008864658B2

(12) United States Patent
Wilkins et al.

(10) Patent No.: US 8,864,658 B2
(45) Date of Patent: Oct. 21, 2014

(54) EXPANDABLE SURGICAL ACCESS PORT

(75) Inventors: Rebecca Ann Wilkins, Royston (GB); Thomas John Hector Copeland, Cambridge (GB); Trevor Beckett, Cambridge (GB); Cormac O'Prey, Stortford (GB); Daniel Brady, Old Windsor (GB); Wai Ting Chan, Cambridge (GB); Daniel Leonard Fuller, Haverhill (GB); Christopher John Silk, Cambridge (GB)

(73) Assignee: Covidien LP, Mansfield, MA (US)

( * ) Notice: Subject to any disclaimer, the term of this patent is extended or adjusted under 35 U.S.C. 154(b) by 335 days.

(21) Appl. No.: 13/297,760

(22) Filed: Nov. 16, 2011

(65) Prior Publication Data

US 2012/0143009 A1 Jun. 7, 2012

Related U.S. Application Data

(63) Continuation-in-part of application No. 13/166,878, filed on Jun. 23, 2011, which is a continuation-in-part of application No. 13/166,875, filed on Jun. 23, 2011.

(60) Provisional application No. 61/420,359, filed on Dec. 7, 2010, provisional application No. 61/372,939, filed on Aug. 12, 2010, provisional application No. 61/375,960, filed on Aug. 12, 2010.

(51) Int. Cl.
*A61B 1/32* (2006.01)
*A61B 17/02* (2006.01)
*A61B 17/34* (2006.01)

(52) U.S. Cl.
CPC ..... *A61B 17/3423* (2013.01); *A61B 2017/0225* (2013.01); *A61B 17/0218* (2013.01); *A61B 2017/3488* (2013.01); *A61B 17/3439* (2013.01); *A61B 17/3431* (2013.01); *A61B 2017/3427* (2013.01)
USPC ............................ 600/201; 600/208; 600/215

(58) Field of Classification Search
CPC ........... A61B 17/0206; A61B 17/0293; A61B 2019/2215; A61B 2017/0225; A61B 2017/3427; A61B 17/3423; A61B 17/0218; A61B 17/3431; A61B 17/3488; A61B 17/3439
See application file for complete search history.

(56) References Cited

U.S. PATENT DOCUMENTS

| 1,780,912 A | 11/1930 | Gau |
| 1,810,466 A | 6/1931 | Deutsch |

(Continued)

FOREIGN PATENT DOCUMENTS

| DE | 10001695 | 2/2001 |
| DE | 102009014527 | 9/2010 |

(Continued)

OTHER PUBLICATIONS

EP Search Report 11 25 0163 dated Jul. 6, 2011.

(Continued)

*Primary Examiner* — David Bates
*Assistant Examiner* — Samuel Hanna

(57) ABSTRACT

A method of accessing an internal portion of a patient including the steps of providing an access assembly including an outer frame, an inner member and a flexible member, inserting the inner member through an opening in tissue into a body of a patient with the flexible member extending proximally through the opening in tissue, moving at least a first portion or second portion of the outer member to a select unlocked spread position to enlarge the opening in tissue and the passageway through the flexible member, and subsequently moving the locking member to move the first and second engagement structures into a locking position to lock the first portion in the select spread position.

21 Claims, 11 Drawing Sheets

(56) References Cited

U.S. PATENT DOCUMENTS

| | | | |
|---|---|---|---|
| 2,313,164 A | 3/1943 | Nelson |
| 2,541,516 A | 2/1951 | Ivory et al. |
| 2,812,758 A | 11/1957 | Blumenschein |
| 3,782,370 A | 1/1974 | McDonald |
| 3,807,393 A | 4/1974 | McDonald |
| 3,965,890 A | 6/1976 | Gauthier |
| 4,130,113 A | 12/1978 | Graham |
| 4,263,899 A | 4/1981 | Burgin |
| 4,553,537 A | 11/1985 | Rosenberg |
| 5,007,900 A | 4/1991 | Picha et al. |
| 5,052,374 A | 10/1991 | Alvarez-Jacinto |
| 5,080,088 A | 1/1992 | LeVahn |
| 5,125,396 A | 6/1992 | Ray |
| 5,169,387 A | 12/1992 | Kronner |
| 5,231,974 A | 8/1993 | Giglio et al. |
| 5,232,451 A | 8/1993 | Freitas et al. |
| 5,269,754 A | 12/1993 | Rydell |
| 5,279,575 A | 1/1994 | Sugarbaker |
| 5,330,501 A | 7/1994 | Tovey et al. |
| 5,346,484 A | 9/1994 | Van Lindert |
| 5,391,156 A | 2/1995 | Hildwein et al. |
| 5,437,683 A | 8/1995 | Neumann et al. |
| 5,445,615 A | 8/1995 | Yoon |
| 5,460,170 A | 10/1995 | Hammerslag |
| 5,480,410 A | 1/1996 | Cuschieri |
| 5,490,843 A | 2/1996 | Hildwein et al. |
| 5,503,617 A | 4/1996 | Jako |
| 5,520,610 A | 5/1996 | Giglio et al. |
| 5,524,644 A | 6/1996 | Crook |
| 5,556,385 A | 9/1996 | Andersen |
| 5,562,677 A | 10/1996 | Hildwein et al. |
| 5,653,705 A | 8/1997 | De la Torre et al. |
| 5,697,891 A | 12/1997 | Hori |
| 5,728,103 A | 3/1998 | Picha et al. |
| 5,755,660 A | 5/1998 | Tyagi |
| 5,755,661 A | 5/1998 | Schwartzman |
| 5,772,583 A | 6/1998 | Wright et al. |
| 5,776,110 A | 7/1998 | Guy et al. |
| 5,779,629 A | 7/1998 | Hohlen |
| 5,788,630 A | 8/1998 | Furnish |
| 5,803,921 A | 9/1998 | Bonadio |
| 5,810,721 A | 9/1998 | Mueller et al. |
| 5,846,193 A | 12/1998 | Wright |
| 5,875,782 A | 3/1999 | Ferrari et al. |
| 5,879,291 A | 3/1999 | Kolata et al. |
| 5,906,577 A | 5/1999 | Beane et al. |
| 5,908,382 A | 6/1999 | Koros et al. |
| 5,931,778 A | 8/1999 | Furnish |
| 5,935,107 A | 8/1999 | Taylor et al. |
| 5,944,736 A | 8/1999 | Taylor et al. |
| 5,951,466 A | 9/1999 | Segermark et al. |
| 5,951,467 A | 9/1999 | Picha et al. |
| 5,957,835 A | 9/1999 | Anderson et al. |
| 5,967,972 A | 10/1999 | Santilli et al. |
| 5,993,385 A | 11/1999 | Johnston et al. |
| 6,024,736 A | 2/2000 | De la Torre et al. |
| 6,033,362 A | 3/2000 | Cohn |
| 6,033,425 A | 3/2000 | Looney et al. |
| 6,036,641 A | 3/2000 | Taylor et al. |
| 6,048,309 A | 4/2000 | Flom et al. |
| 6,074,380 A | 6/2000 | Byrne et al. |
| 6,113,535 A | 9/2000 | Fox et al. |
| 6,120,436 A | 9/2000 | Anderson et al. |
| 6,132,370 A | 10/2000 | Furnish et al. |
| 6,142,935 A | 11/2000 | Flom et al. |
| 6,159,231 A | 12/2000 | Looney et al. |
| 6,162,172 A | 12/2000 | Cosgrove et al. |
| 6,231,506 B1 | 5/2001 | Hu et al. |
| 6,254,533 B1 | 7/2001 | Fadem et al. |
| 6,254,534 B1 | 7/2001 | Butler et al. |
| 6,283,912 B1 | 9/2001 | Hu et al. |
| 6,309,349 B1 | 10/2001 | Bertolero et al. |
| 6,312,377 B1 | 11/2001 | Segermark et al. |
| 6,331,158 B1 | 12/2001 | Hu et al. |
| 6,332,468 B1 | 12/2001 | Benetti |
| 6,354,995 B1 | 3/2002 | Hoftman et al. |
| 6,361,492 B1 | 3/2002 | Santilli |
| 6,382,211 B1 | 5/2002 | Crook |
| 6,443,957 B1 | 9/2002 | Addis |
| 6,450,983 B1 | 9/2002 | Rambo |
| 6,458,079 B1 | 10/2002 | Cohn et al. |
| 6,500,116 B1 | 12/2002 | Knapp |
| 6,517,563 B1 | 2/2003 | Paolitto et al. |
| 6,547,725 B1 | 4/2003 | Paolitto et al. |
| 6,585,442 B2 | 7/2003 | Brei et al. |
| 6,599,240 B2 | 7/2003 | Puchovsky et al. |
| 6,599,292 B1 | 7/2003 | Ray |
| 6,616,605 B2 | 9/2003 | Wright et al. |
| 6,652,454 B2 | 11/2003 | Hu et al. |
| 6,723,044 B2 | 4/2004 | Pulford et al. |
| 6,730,021 B2 | 5/2004 | Vassiliades, Jr. et al. |
| 6,730,022 B2 | 5/2004 | Martin et al. |
| 6,746,396 B1 | 6/2004 | Segermark et al. |
| 6,746,467 B1 | 6/2004 | Taylor et al. |
| 6,814,078 B2 | 11/2004 | Crook |
| 6,814,700 B2 | 11/2004 | Mueller et al. |
| 6,840,951 B2 | 1/2005 | De la Torre et al. |
| 6,846,287 B2 | 1/2005 | Bonadio et al. |
| 6,958,037 B2 | 10/2005 | Ewers et al. |
| 7,033,319 B2 | 4/2006 | Pulford et al. |
| 7,052,454 B2 | 5/2006 | Taylor |
| 7,144,368 B2 | 12/2006 | Larson et al. |
| 7,147,599 B2 | 12/2006 | Phillips et al. |
| 7,179,225 B2 | 2/2007 | Shluzas et al. |
| 7,195,592 B2 | 3/2007 | Ravikumar et al. |
| 7,220,228 B2 | 5/2007 | Hu et al. |
| 7,226,451 B2 | 6/2007 | Shluzas et al. |
| 7,229,408 B2 | 6/2007 | Douglas et al. |
| 7,238,154 B2 | 7/2007 | Ewers et al. |
| 7,261,688 B2 | 8/2007 | Smith et al. |
| 7,270,632 B2 | 9/2007 | Santilli |
| 7,300,399 B2 | 11/2007 | Bonadio et al. |
| 7,344,495 B2 | 3/2008 | Ravikumar et al. |
| 7,387,126 B2 | 6/2008 | Cox et al. |
| 7,393,322 B2 | 7/2008 | Wenchell |
| 7,473,222 B2 | 1/2009 | Dewey et al. |
| 7,507,202 B2 | 3/2009 | Schoellhorn |
| 7,507,235 B2 | 3/2009 | Keogh et al. |
| 7,537,564 B2 | 5/2009 | Bonadio et al. |
| 7,540,839 B2 | 6/2009 | Butler et al. |
| 7,559,893 B2 | 7/2009 | Bonadio et al. |
| 7,566,302 B2 | 7/2009 | Schwer |
| 7,585,277 B2 | 9/2009 | Taylor et al. |
| 7,594,888 B2 | 9/2009 | Raymond et al. |
| 7,650,887 B2 | 1/2010 | Nguyen et al. |
| 2001/0002429 A1 | 5/2001 | Hu et al. |
| 2001/0020121 A1 | 9/2001 | Hu et al. |
| 2001/0041827 A1 | 11/2001 | Spence et al. |
| 2002/0004628 A1 | 1/2002 | Hu et al. |
| 2002/0095139 A1 | 7/2002 | Keogh et al. |
| 2002/0099269 A1 | 7/2002 | Martin et al. |
| 2002/0099271 A1 | 7/2002 | Knapp |
| 2002/0137989 A1 | 9/2002 | Clem et al. |
| 2003/0191371 A1 | 10/2003 | Smith et al. |
| 2004/0049099 A1 | 3/2004 | Ewers et al. |
| 2004/0054353 A1* | 3/2004 | Taylor ............................ 606/1 |
| 2004/0059192 A1 | 3/2004 | Cartier et al. |
| 2004/0225195 A1 | 11/2004 | Spence et al. |
| 2005/0096508 A1 | 5/2005 | Valentini et al. |
| 2005/0137460 A1 | 6/2005 | Bertolero |
| 2005/0171403 A1 | 8/2005 | Paolitto et al. |
| 2005/0228232 A1 | 10/2005 | Gillinov et al. |
| 2005/0267336 A1 | 12/2005 | Bertolero et al. |
| 2005/0283050 A1 | 12/2005 | Gundlapalli et al. |
| 2006/0004261 A1 | 1/2006 | Douglas |
| 2006/0089537 A1 | 4/2006 | Schoellhorn |
| 2006/0106416 A1 | 5/2006 | Raymond et al. |
| 2006/0129165 A1 | 6/2006 | Edoga et al. |
| 2006/0149137 A1 | 7/2006 | Pingleton et al. |
| 2006/0149306 A1 | 7/2006 | Hart et al. |
| 2006/0155170 A1 | 7/2006 | Hanson et al. |
| 2007/0027364 A1 | 2/2007 | Schwer |
| 2007/0073110 A1 | 3/2007 | Larson et al. |
| 2007/0299314 A1* | 12/2007 | Bertolero et al. ............. 600/201 |

(56) References Cited

U.S. PATENT DOCUMENTS

| | | |
|---|---|---|
| 2008/0132766 A1 | 6/2008 | Dant et al. |
| 2008/0234550 A1 | 9/2008 | Hawkes et al. |
| 2009/0204067 A1 | 8/2009 | Abu-Halawa |
| 2009/0265941 A1 | 10/2009 | Kurrus |
| 2009/0299148 A1 | 12/2009 | White et al. |
| 2010/0210916 A1 | 8/2010 | Hu et al. |
| 2010/0234689 A1 | 9/2010 | Wagner et al. |
| 2010/0261970 A1 | 10/2010 | Shelton, IV et al. |
| 2011/0021879 A1 | 1/2011 | Hart et al. |

FOREIGN PATENT DOCUMENTS

| | | |
|---|---|---|
| EP | 0177177 | 4/1986 |
| EP | 2179699 | 4/2010 |
| EP | 2 228 014 | 9/2010 |
| EP | 2 228 024 | 9/2010 |
| EP | 2 238 931 A1 | 10/2010 |
| EP | 2 422 725 | 2/2012 |
| EP | 2417922 | 2/2012 |
| EP | 2 462 883 | 6/2012 |
| GB | 2275420 | 8/1994 |
| JP | H10-507653 | 7/1998 |
| WO | WO95/00197 | 1/1995 |
| WO | WO95/15715 | 6/1995 |
| WO | WO96/05773 | 2/1996 |
| WO | WO 01/08563 A2 | 2/2001 |
| WO | WO03/034908 | 5/2003 |
| WO | WO-03/034908 | 5/2003 |
| WO | WO-2005/089655 | 9/2005 |
| WO | WO2005/089655 | 9/2005 |
| WO | WO2010/042913 | 4/2010 |
| WO | WO 2010/136805 | 12/2010 |
| WO | WO 2011/079374 | 7/2011 |

OTHER PUBLICATIONS

EP Search Report 11 25 0164 dated Aug. 6, 2011.
EP Search Report EP 11 25 0719 dated Nov. 16, 2011.
EP Search Report EP 11 18 9987 dated Feb. 15, 2012.
EP Search Report EP 12160423.5 dated Jun. 25, 2012.
EP Search Report EP 12 15 4733 dated Jan. 14, 2014.
Japanese Office Action dated Feb. 28, 2014.

\* cited by examiner

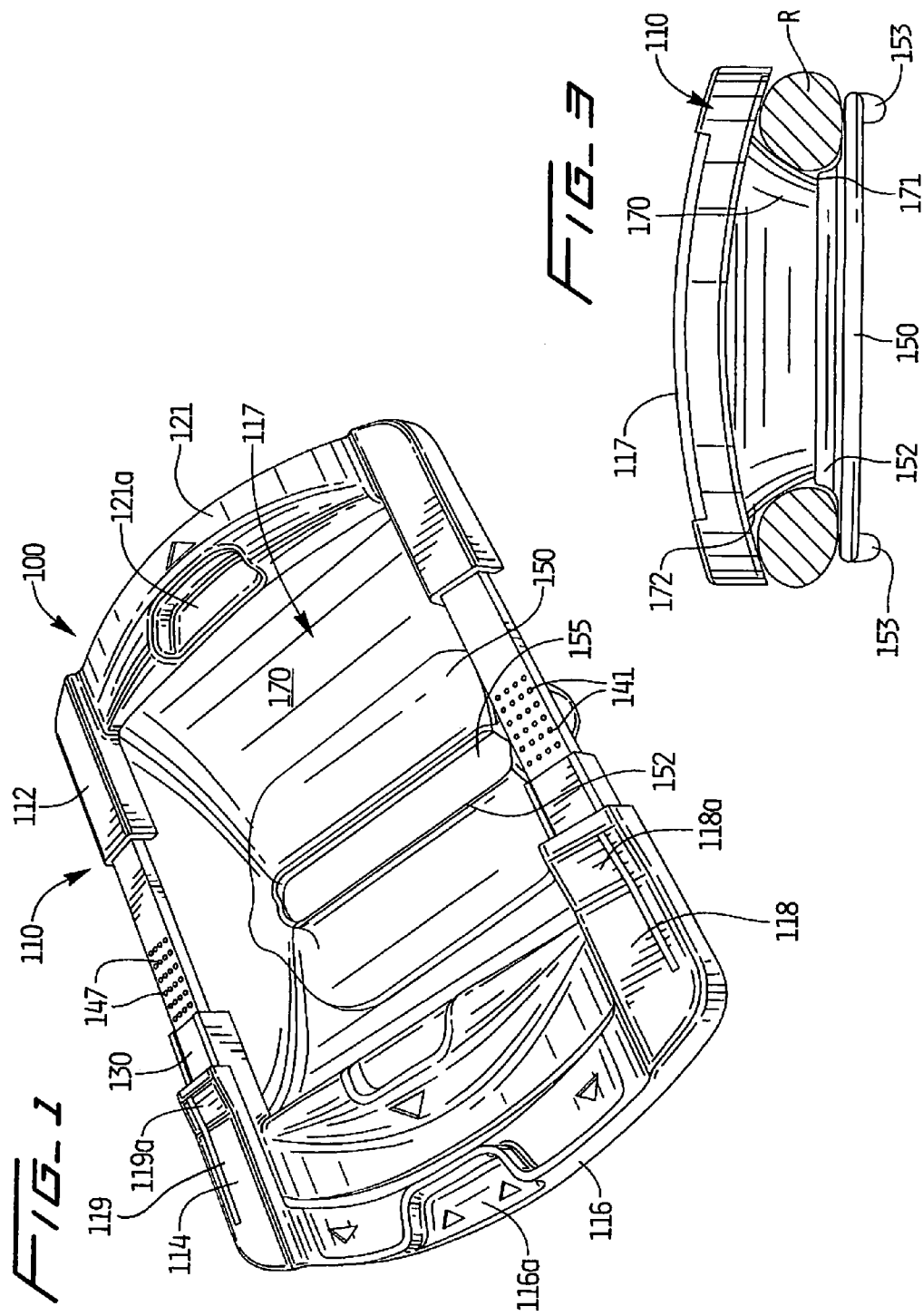

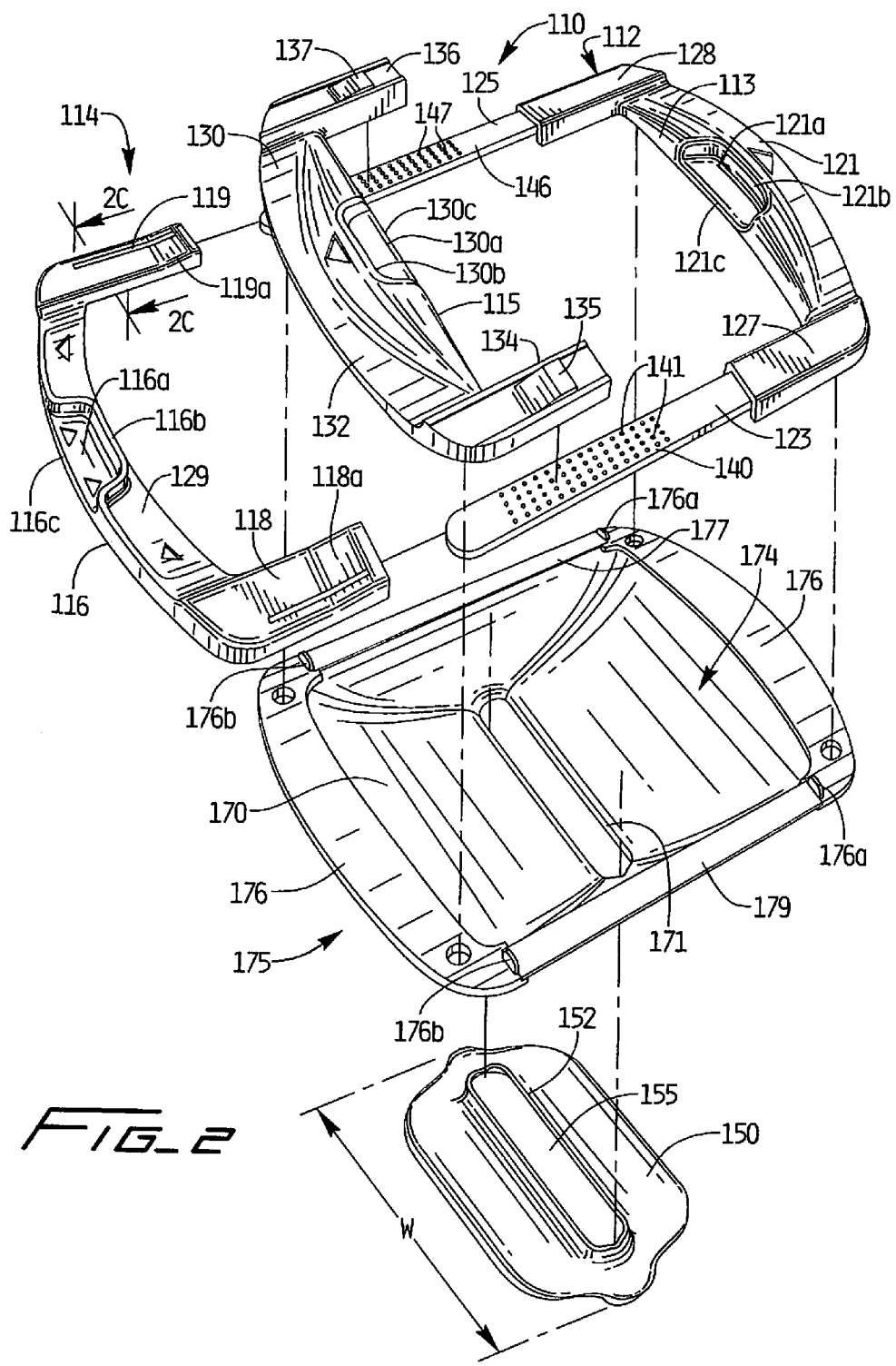
FIG_2

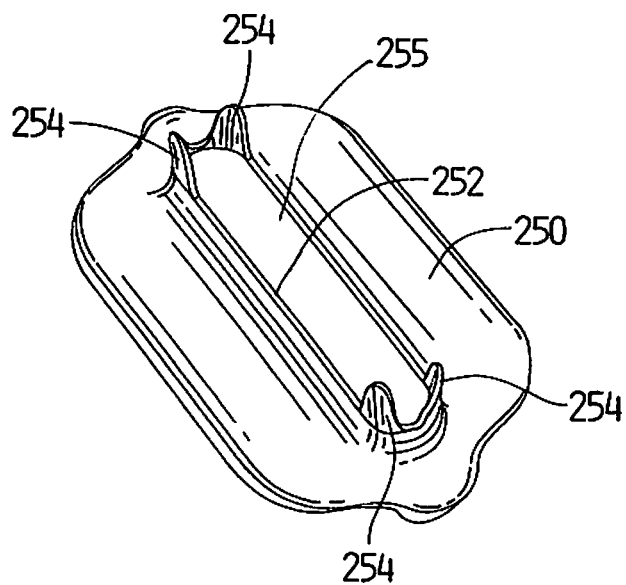
FIG_2B
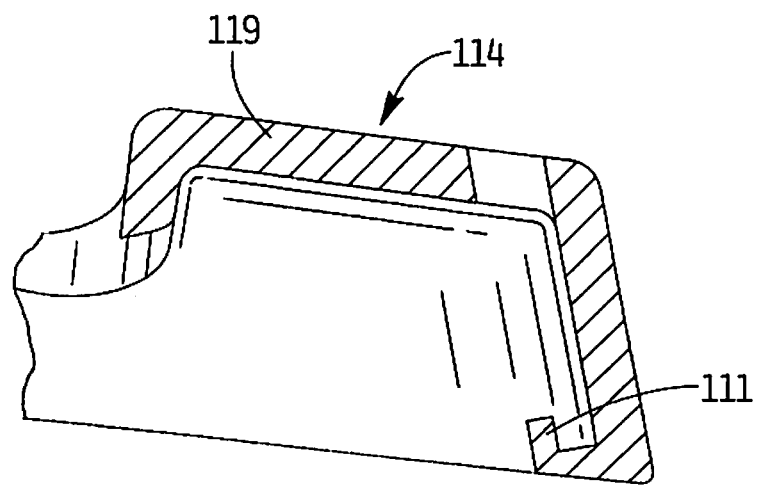
FIG_2C

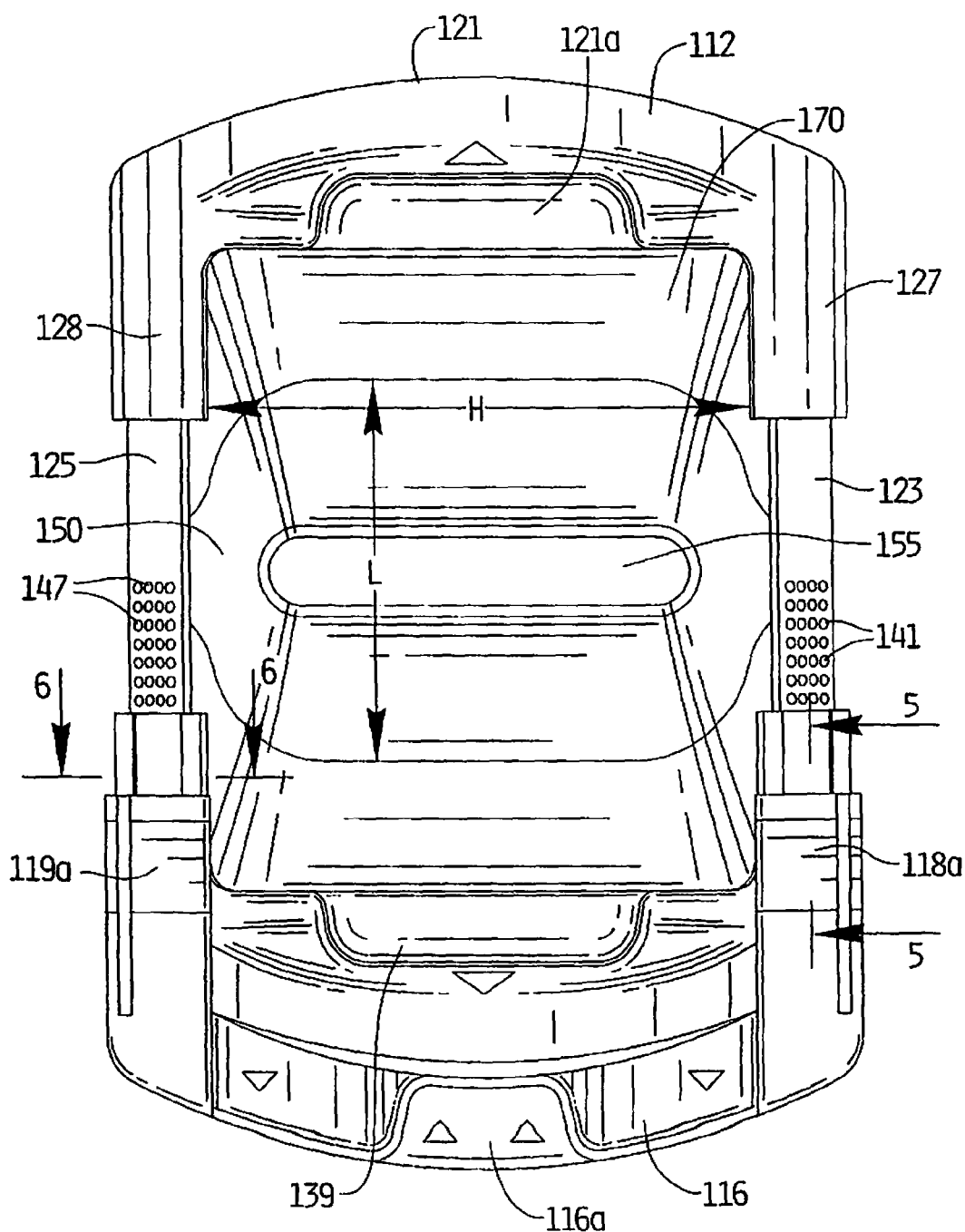

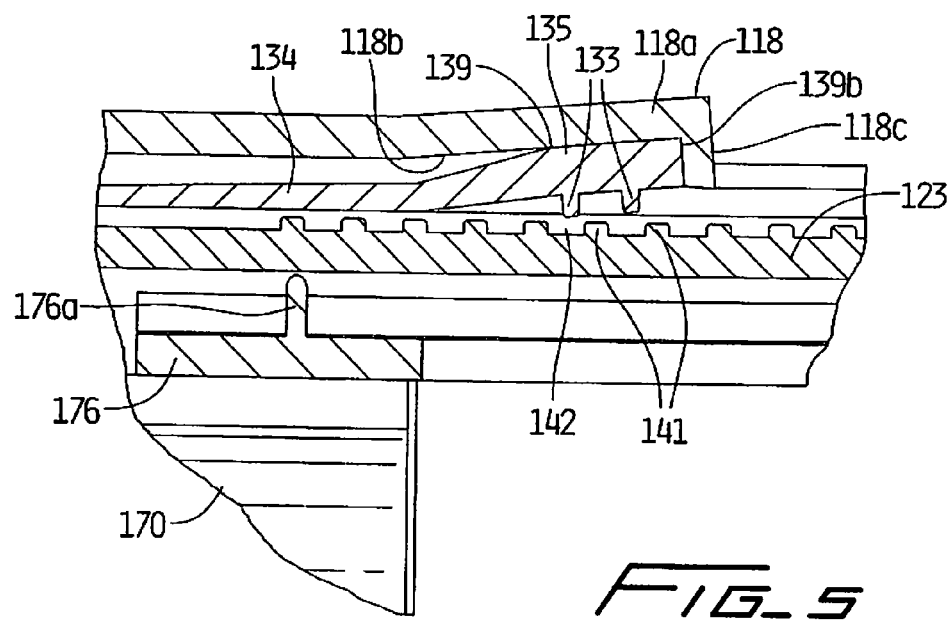
FIG_5
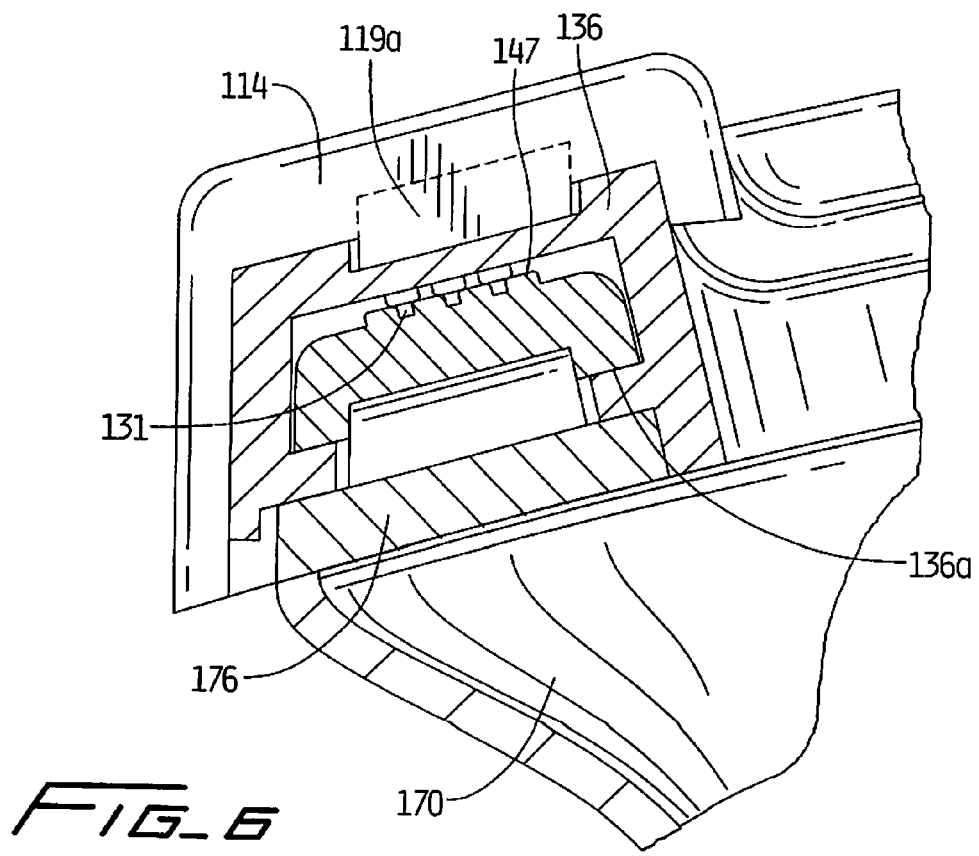
FIG_6

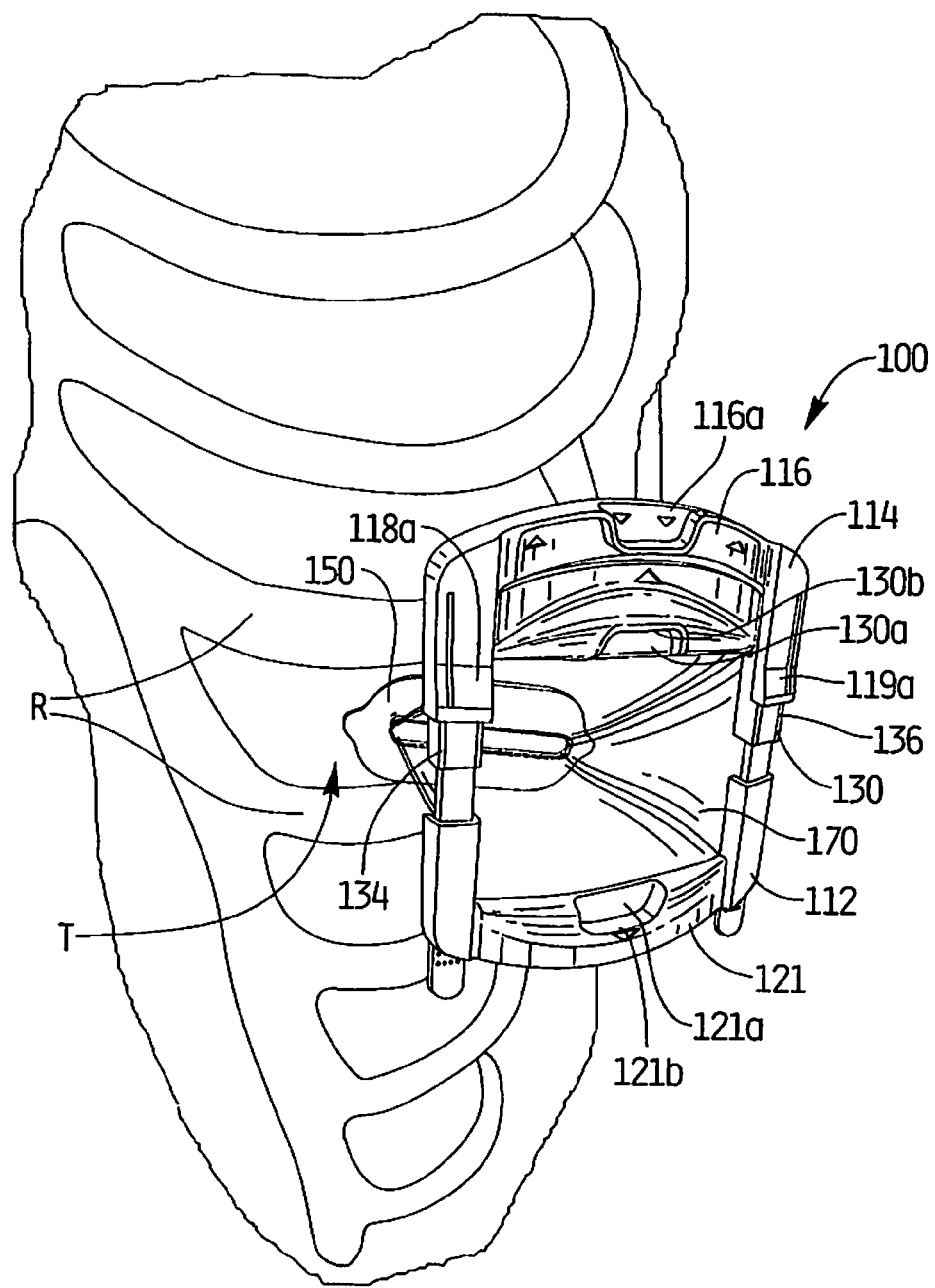
FIG_8

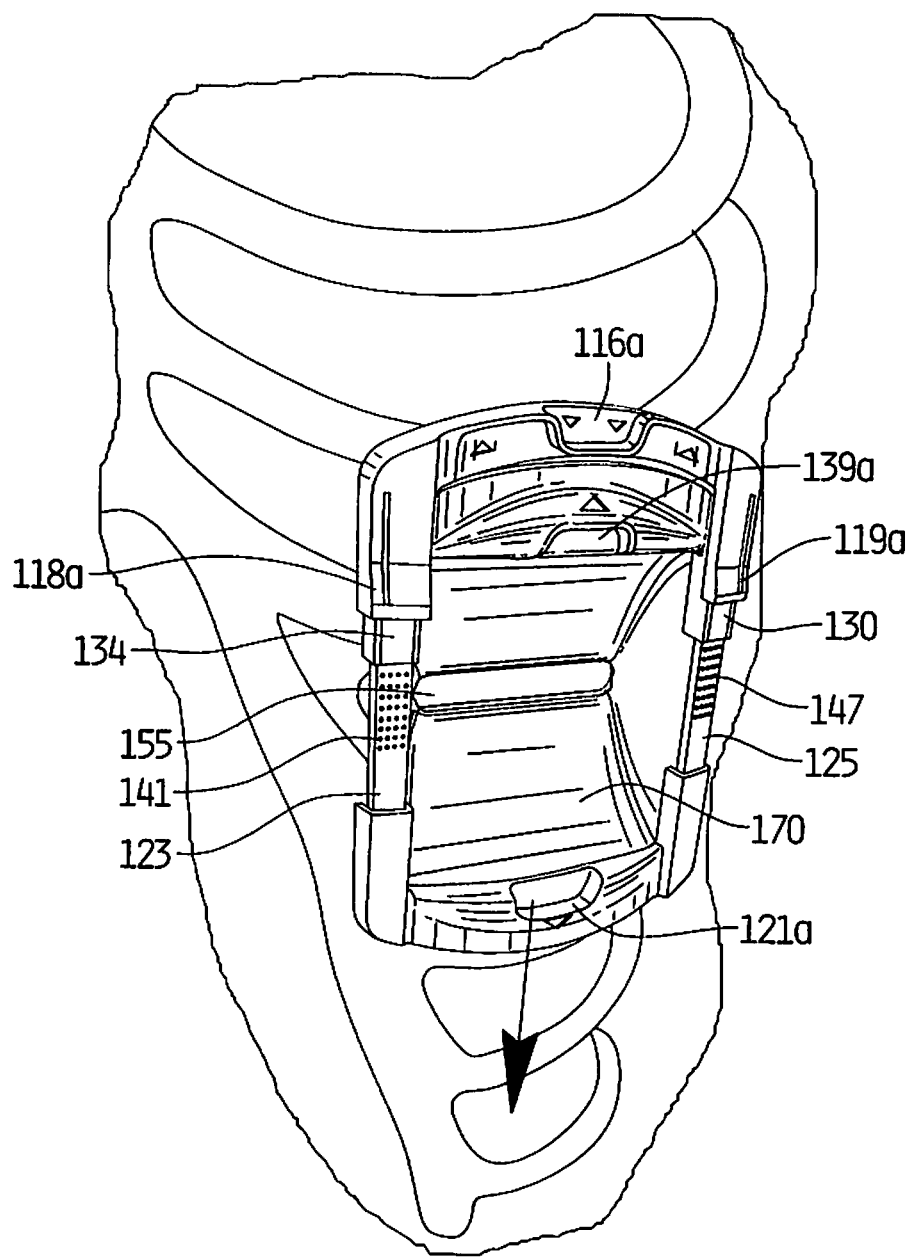
FIG_9

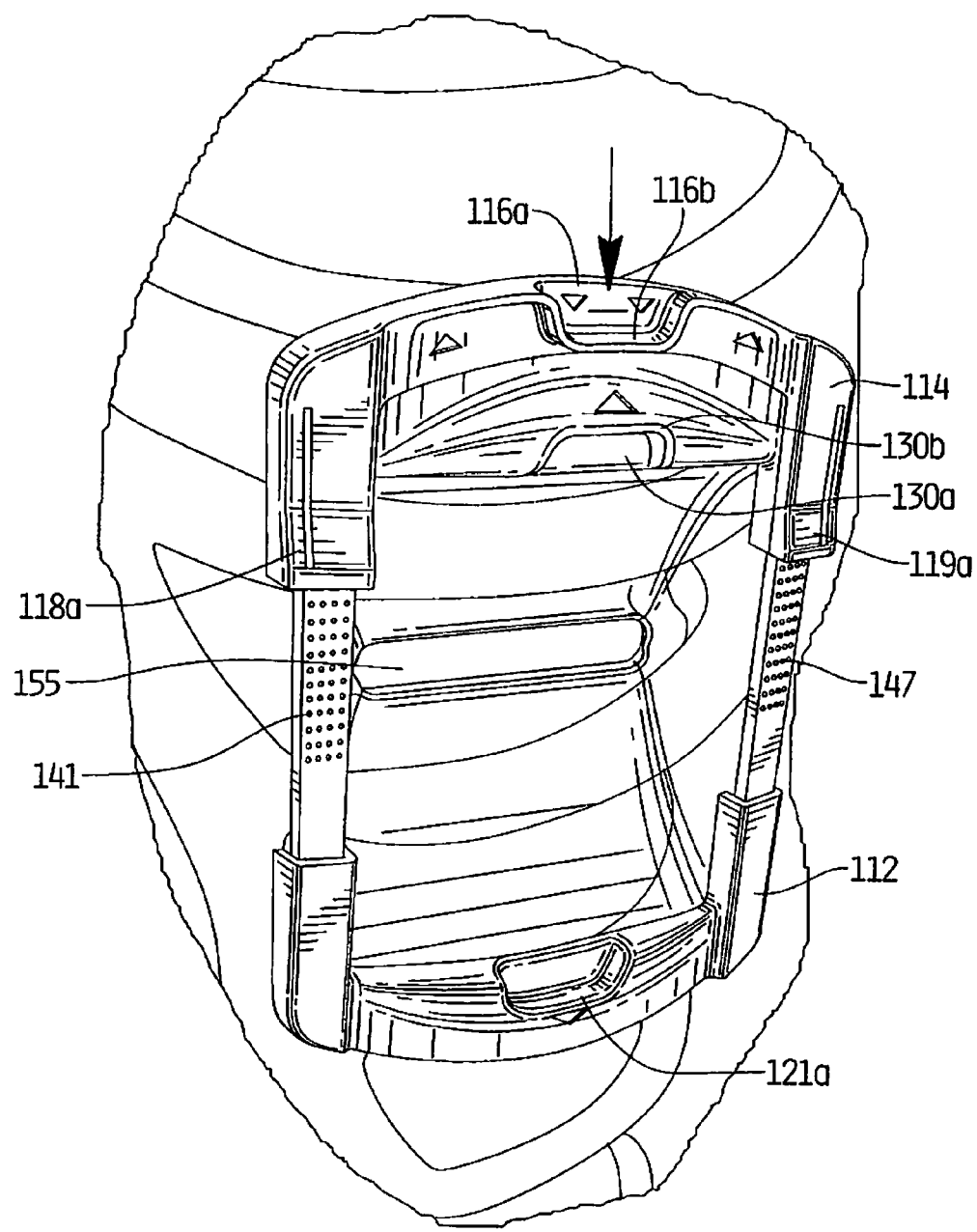

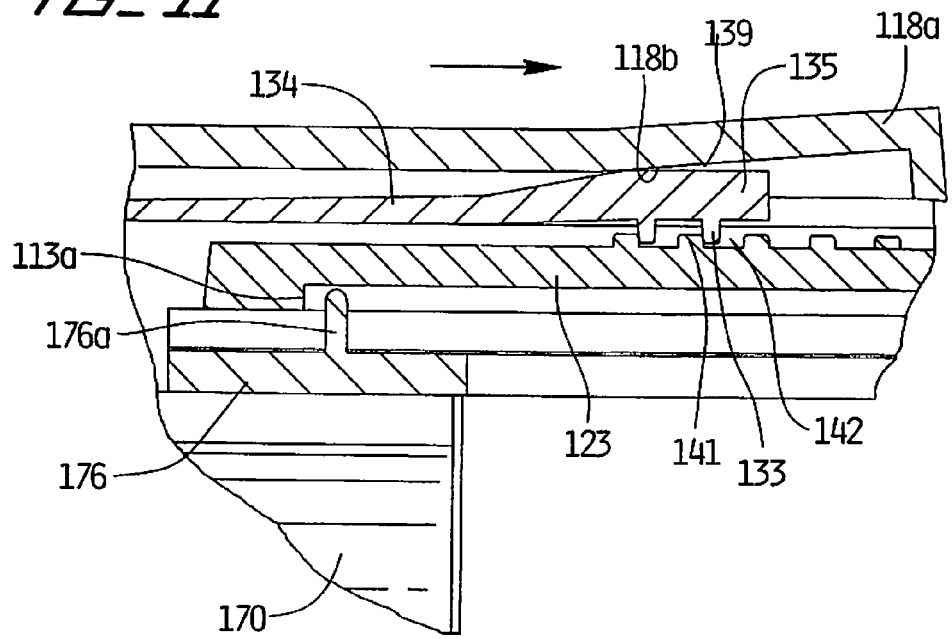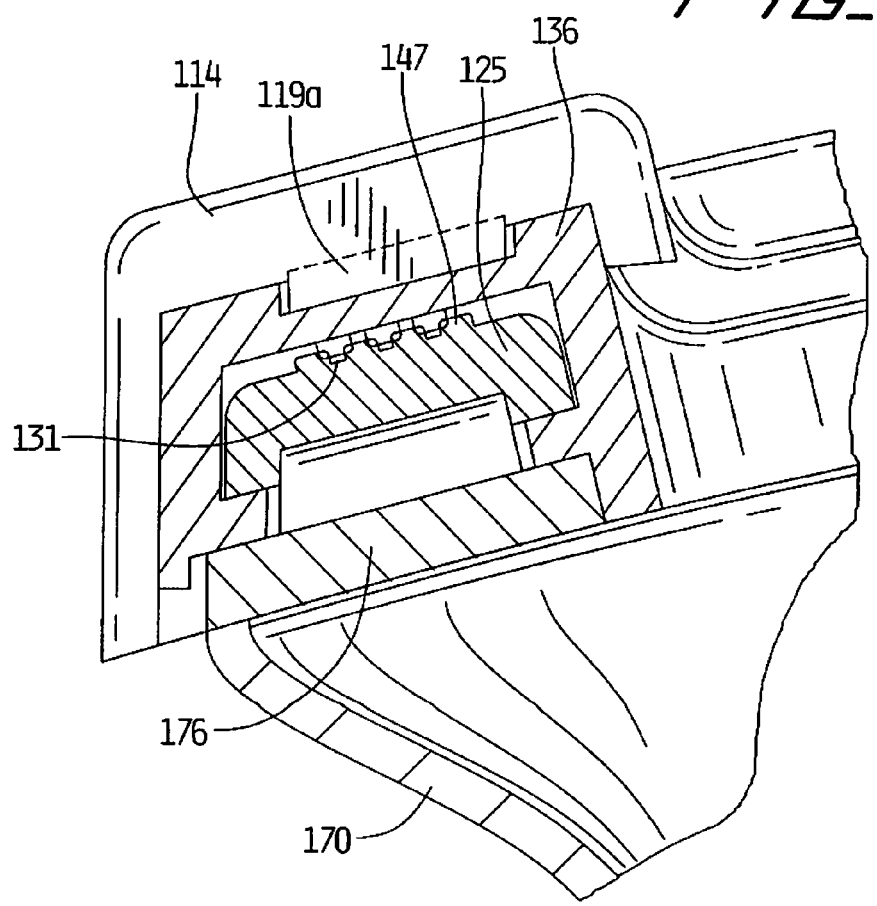

EXPANDABLE SURGICAL ACCESS PORT

This application claims priority from provisional application Ser. No. 61/420,359, filed Dec. 7, 2010, and is a continuation-in-part of application Ser. No. 13/166,878, filed Jun. 23, 2011, which claims priority from provisional application Ser. No. 61/372,939, filed Aug. 12, 2010, and is a continuation-in-part of application Ser. No. 13/166,875, filed Jun. 23, 2011, which claims priority from provisional application Ser. No. 61/372,960, filed Aug. 12, 2010. The entire contents of each of these applications are incorporated herein by reference.

BACKGROUND

1. Technical Field

The present disclosure relates generally to devices and techniques for performing surgical procedures. More particularly, the present disclosure relates to an expandable access device for minimally invasive surgery.

2. Background of the Related Art

In an effort to reduce trauma and recovery time, many surgical procedures are performed through small openings in the skin, such as an incision or a natural body orifice. For example, these procedures include laparoscopic procedures, which are generally performed within the confines of a patient's abdomen, and thoracic procedures, which are generally performed within a patient's chest cavity.

Specific surgical instruments have been developed for use during such minimally invasive surgical procedures. These surgical instruments typically include an elongated shaft with operative structure positioned at a distal end thereof, such as graspers, clip appliers, specimen retrieval bags, etc.

During minimally invasive procedures, the clinician creates an opening in the patient's body wall, oftentimes by using an obturator or trocar, and thereafter positions an access assembly within the opening. The access assembly includes a passageway extending therethrough to receive one or more of the above-mentioned surgical instruments for positioning within the internal work site, e.g. the body cavity.

During minimally invasive thoracic procedures, an access assembly is generally inserted into a space located between the patient's adjacent ribs that is known as the intercostal space, and then surgical instruments can be inserted into the internal work site, i.e. thoracic cavity, through the passageway in the access assembly.

In the interests of facilitating visualization, the introduction of certain surgical instruments, and/or the removal of tissue specimens during minimally invasive thoracic procedures, it may be desirable to spread the tissue adjacent the ribs defining the intercostal space. Additionally, during these procedures, firm, reliable placement of the access assembly is desirable to allow the access assembly to withstand forces that are applied during manipulation of the instrument(s) inserted therethrough. However, reducing patient trauma during the procedure, discomfort during recovery, and the overall recovery time remain issues of importance. Thus, there exists a need for a thoracic access port which minimizes post operative patient pain while enabling atraumatic retraction of tissue and which does not restrict access to the body cavity, as well as facilitates retrieval of tissue specimens from the body cavity and aids visualization of and through the incision.

SUMMARY

In accordance with one aspect of the present disclosure, a method of accessing an internal portion of a patient is provided. The method includes the step of providing an access assembly including an outer frame positionable outside a patient and defining an opening therein, and including first and second portions, and a locking portion, wherein at least one of the first and second portions is movable with respect to the other portion to adjust the opening and the opening is dimensioned to receive a surgical instrument therethrough. The second portion has a first engagement structure and a second engagement structure. The access assembly further includes an inner member positionable within a patient and a flexible member extending between the inner member and outer frame and operatively associated with the outer frame, and having a passageway to receive the surgical instrument therethrough, wherein movement of the outer frame adjusts tension on the flexible member. The method further includes the steps of inserting the inner member through an opening in tissue into a body of a patient with the flexible member extending proximally through the opening in tissue, moving at least one of the first and second portions of the outer frame to a select unlocked spread position to enlarge the opening in tissue and the passageway through the flexible member, and subsequently moving the locking member to move the first and second engagement structures into a locking position to lock the first and second portions in the select spread position.

The method may further include the step of introducing a surgical instrument through the opening in the outer frame and the passageway in the flexible member.

The step of moving the locking member to move the first and second engagement structures into a locking position can include the step of camming the first and second engagement structures into engagement with first and second surfaces of the outer frame.

In some embodiments, the step of moving at least one of the first and second portions can include the step of sliding the first portion in a direction away from the second portion. The step of moving the locking member can include the step of sliding the locking member toward the first portion.

A specimen retrieval apparatus can be inserted through the passageway in the flexible member. The step of inserting the inner member can include the step of inserting the inner member into a thoracic cavity of a patient. The inner member can be folded for insertion through the tissue opening.

In another aspect, the present disclosure provides a method of accessing a thoracic cavity of a patient for performing minimally invasive thoracic surgery comprising the steps of providing an access assembly including an outer frame defining an opening therein and including a locking portion and first and second portions relatively movable to adjust the opening. The opening is dimensioned to receive a surgical instrument therethrough to access the thoracic cavity, and the second portion has a first engagement structure and a second engagement structure spaced from the first engagement structure. The access assembly further includes a flexible member extending distally from the outer frame and having a passageway dimensioned to receive the surgical instrument therethrough to access the thoracic cavity. The method further includes the steps of moving at least one of the first and second portions of the outer frame to a select unlocked spread position to enlarge the opening in tissue and the passageway through the flexible member, and moving the locking member to move the first and second engagement structures into a locking position in locking engagement with the first portion to lock the outer frame in the select spread position.

In some embodiments, the access assembly includes an inner member, and the flexible member extends proximally from the inner member, and the method further includes the step of inserting the inner member through the opening in tissue and intercostal space into the thoracic cavity of a patient with the flexible member extending proximally through the opening in tissue.

In some embodiments, the method includes the step of introducing a surgical instrument through the passageway into the thoracic cavity. The instrument can be a specimen retrieval apparatus.

In some embodiments, the step of moving the locking member to move the first and second engagement structures into a locking position includes the step of camming the first and second engagement structures into engagement with first and second surfaces on the first portion. The step of moving at least one of the first and second portions can include the step of sliding the first portion in a direction away from the second portion. The step of moving the locking member can include the step of sliding the second portion toward the locking member.

In some embodiments, the step of inserting the inner member includes the step of folding the inner member for insertion through the tissue opening.

The step of moving at least one of the first and second portions can include the step of placing one or more fingers in an indentation formed in the first portion. The step of moving the locking member can include the step of placing one or more fingers in an indentation formed in the locking member. The step of moving the locking member can include the step of pressing the locking member and second portion toward each other.

BRIEF DESCRIPTION OF THE DRAWINGS

Various embodiments of the subject access port are described herein with reference to the drawings wherein:

FIG. 1 is a perspective view of one embodiment of the surgical access port of the present disclosure;

FIG. 2 is an exploded view of the access port of FIG. 1;

FIG. 2B is a perspective view of an alternate embodiment of the inner frame;

FIG. 2C is a cross-sectional view taken along line 2C-2C of FIG. 2;

FIG. 3 is a side view of the access port of FIG. 1;

FIG. 4 is a top view of the access port of FIG. 1 shown in a spread (expanded) position;

FIG. 5 is a cross-sectional view taken along line 5-5 of FIG. 4 and showing the locking mechanism in the unlocked position;

FIG. 6 is a cross-sectional view taken along line 6-6 of FIG. 4;

FIG. 8 is a perspective view illustrating a patient's skeletal structure with the surgical access port of FIG. 1 positioned within the intercostal space defined between adjacent ribs in accordance with the present disclosure, and shown in the initial non-expanded position;

FIG. 9 is a view similar to FIG. 8 showing the access port in an expanded and unlocked position;

FIG. 10 is a view similar to FIG. 9 showing the access port in a further expanded portion and the locking member in the locking position to retain the access port in the expanded position;

FIG. 11 is a cross-sectional view similar to FIG. 5 showing engagement of the locking structure to retain the access port in the expanded position; and FIG. 12 is a cross-sectional view similar to FIG. 6 showing engagement of the locking structure.

DETAILED DESCRIPTION

Figure 2A:
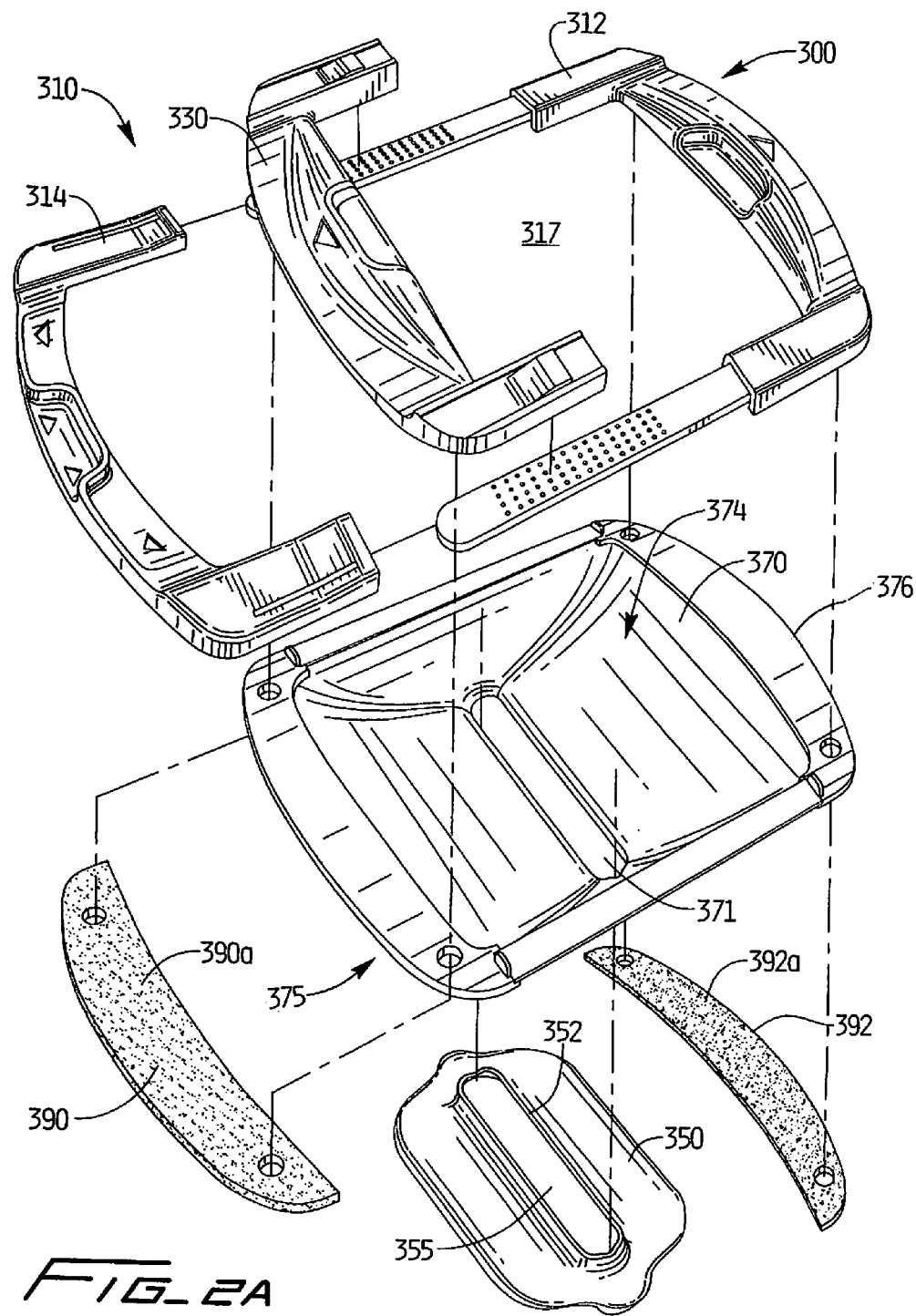
FIG. 2A is an exploded view of an alternate embodiment of the access port.
Figure 7:
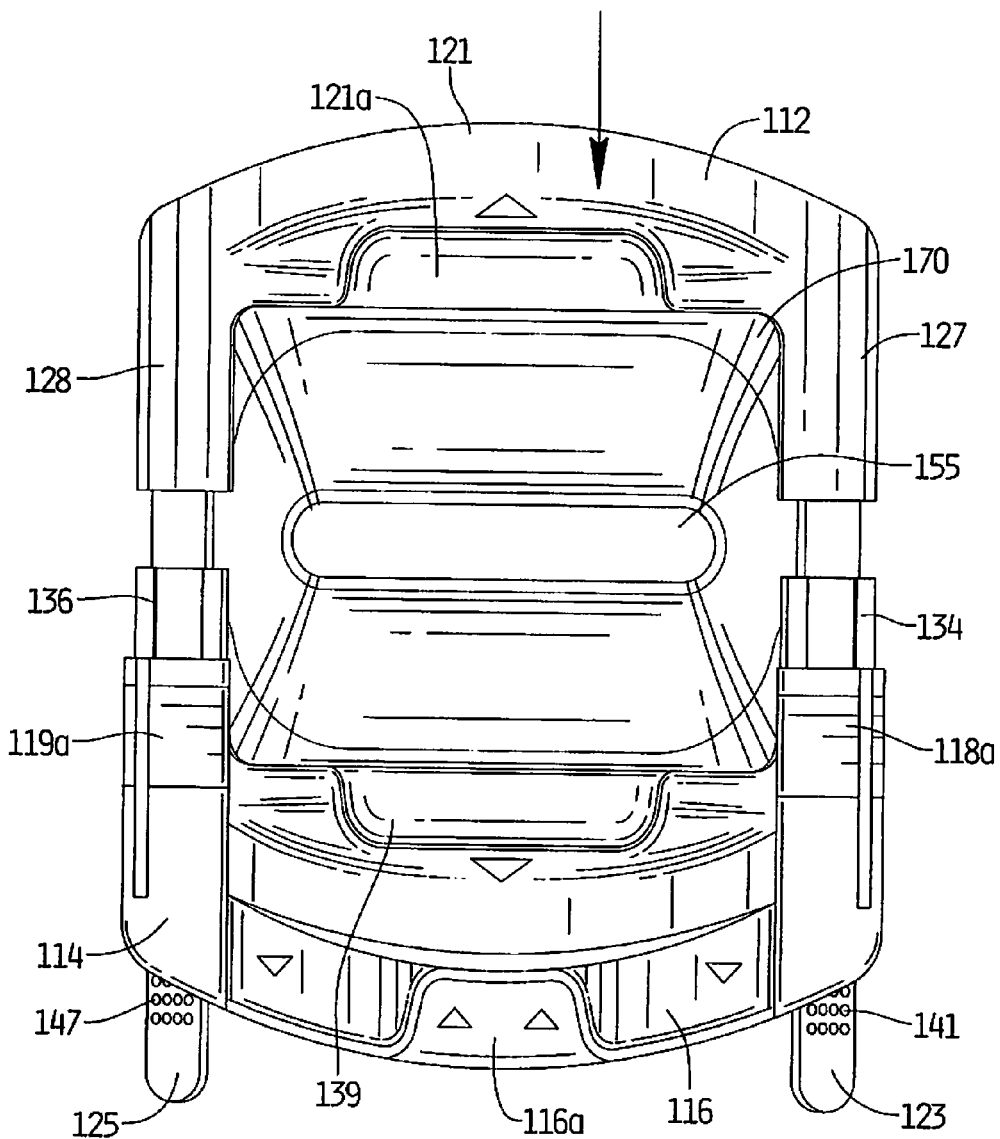
FIG. 7 is a top view similar to FIG. 4 showing the access port in the non-expanded position.

Various embodiments of the presently disclosed access assembly, or access port, and methods of using the same, will now be described in detail with reference to the drawings wherein like references numerals identify similar or identical elements. In the drawings, and in the following description, the term "proximal" refers to the end of the access port, or component thereof, that is closer to the clinician and the term "distal" refers to the end that is further from the clinician, as is traditional and conventional in the art. It should also be understood that the term "minimally invasive procedure" is intended to include surgical procedures through small openings/incisions performed within a confined space such as the thoracic cavity.

Referring now to FIGS. 1 and 2, an embodiment of the presently disclosed surgical access port, generally identified by the reference numeral 100, is depicted as a thoracic port 100 that is configured and dimensioned for insertion into the intercostal space located between the adjacent ribs "R" (FIG. 8) of a patient in order to allow for the insertion and manipulation of one or more surgical instruments within the thoracic cavity. However, it is also envisioned that access port 100 may be configured and dimensioned to provide access to a variety of other internal body cavities and/or tissues. Access port 100 may be formed from any suitable biocompatible material of strength suitable for the purpose described herein, including, but not being limited to, polymeric materials.

The access port 100 is configured and dimensioned to extend into a body cavity, e.g., the thoracic cavity "T" (FIG. 8), through the intercostal space, and with reference to FIGS. 1 and 2, generally includes an outer or proximal frame 110 having first and second frame portions 112, 130 and a locking member or locking portion 114. A flexible member 170, e.g. membrane 170, is coupled to outer frame 110 and extends distally therefrom. The distal end 171 of the flexible member 170 is attached to an inner or distal frame 150. The outer frame 110 is movable between various spread positions to widen the passageway for insertion of instrumentation. More specifically, first and second portions 112 and 130 of frame 110 are relatively slidable to increase the distance between respective inner end walls 113, 115, and to increase the size of the opening 117 in the outer frame 110. The sliding of portions 112 and 130 applies tension to the flexible member 170 to retract tissue adjacent the incision in the patient to widen the access opening in the manner described below. It should be appreciated that although as described below both the first and second portions 112, 130 are slidable, it is also contemplated that only the first portion 112 (or lower portion as viewed in the orientation of FIG. 1) is slidable with respect to the second (upper) portion 130, or that only the second portion 130 (the upper portion as viewed in the orientation of FIG. 1) is slidable with respect to the first (lower) portion. Thus, the term relatively slidable includes one or both of the first and second portions 112, 130 moving relative to the other portion.

It should be understood that the use of the term first and second portions and locking portions or members contemplates an assembly of several components or a unitary assembly.

As shown, the frame 110 is substantially rectangular in shape with a substantially rectangular opening 117. As can be appreciated, other shaped frames and openings are also contemplated. Note also that preferably the shape is elongated, e.g. has a length greater than its width H (see FIG. 4), at least in its spread position, which better conforms to the shape of the incision to facilitate removal of tissue specimens through the access port 100. By way of example, the frame 110 can have a width of about 4.7 inches and a length which changes from about 4.3 inches to about 5.9 inches. Other dimensions are also contemplated.

Inner member or inner frame 150 has an elongated opening 155 therethrough for passage of surgical instrumentation. The inner member 150 also has a nerve protecting wall or lip 152 extending along the opening 155, and preferably substantially surrounding the opening, and extending upwardly toward outer frame 110. The lip facilitates attachment of the flexible membrane 170 thereto. The inner member 150 is preferably composed of a substantially rigid material to provide anchoring of the access port while of sufficient flexibility to be bent or reconfigured for insertion as described below and sufficiently flexible to fit the curvature of the ribs of the intercostal space. In one embodiment by way of example, the inner frame has a length L (FIG. 4) of about 2.3 inches and a width W (FIG. 2) of about 5.1 inches, although other dimensions are also contemplated. The opening 155 is preferably non-circular in configuration, e.g. oval like in configuration. Other configurations are also contemplated. In the illustrated embodiment, the inner frame 150 is positioned transverse to the direction of movement of the outer frame 110. Consequently, the longer dimension of the opening 155 in inner frame 150 is transverse to the longer dimension of the passageway 117 of the outer frame 110. Stated another way, the outer frame 110, at least in its expanded position, has a length exceeding its width, the inner frame 150 has a width exceeding its length, and the lengthwise dimension of the outer frame 110 is aligned with the lengthwise dimension of the inner frame 150.

Inner member 150 includes tabs 153 extending distally from a bottom surface (see FIG. 3). The tabs 153 facilitate removal by providing a gripping surface for a surgical tool for removal of the inner member 150 at the end of the surgical procedure. They also facilitate grasping by the surgeon if desirable. The tabs can include a flared distal end and/or texture to facilitate grasping.

In the alternate embodiment of FIG. 2B, the inner frame 250 has a lip 252 surrounding opening 255 and having a plurality of proximally extending tabs 254 to increase the attachment area, e.g. weld area, for the flexible member 170. As shown, two tabs 254 are positioned on each end of the opening to increase the attachment area at the corners. In all other respects, inner frame 250 is identical to inner frame 150 of FIG. 2.

Flexible member 170 is generally funnel shaped and is coupled at its distal end 171 (see FIG. 3) to lip 152 of inner member 150 and extends proximally therefrom. Proximal end 172 of flexible member 170 can be coupled to end walls 113, 115 (or their lower surfaces) of outer frame 110 or alternatively to end supports 176, 178 discussed below, to isolate tissue surrounding access port 100 from the passageway 174 extending therethrough, thus reducing the risk of tissue damage and/or infection during the surgical procedure. The flexible member 170 can be attached by various methods such as welding, gluing, and thermal bonding. It is envisioned that flexible member 170 is configured for soft tissue retraction. It is also envisioned that flexible member 170 be of sufficient elasticity to permit retraction of a wide range of tissue thicknesses since there may be a wide range of tissue thicknesses among different patients. It is also envisioned that flexible member 170 is of sufficient strength to prevent accidental tearing and/or puncture by surgical instrumentation inserted through access port 100. Additionally, it is envisioned that flexible membrane 170 be made from a bio-compatible material to reduce the incidents of adverse reaction by a patient upon contact with the patient's tissue. Flexible member 170 can be in the form of a flexible membrane. Flexible member 170 may also be made of a transparent material to allow the surgeon to better visualize the surgical site and surrounding tissue. Flexible member can be composed of polyurethane, although other materials such as silicone are also contemplated. It can be composed of a single member, a single member folded over and the edges attached forming a single seam, or alternatively two or more members attached together. For example, a two panel design with two seams or a four panel design with four seams, two on each side, can be utilized, with the flexible panels welded along the seam.

Flexible member 170, in the embodiment shown in FIG. 2, can be supported by a base 175. Base 175 includes end supports 176, 178, preferably composed of a polymeric material, and elongated membrane tensioning bands 177, 179, shown in substantially parallel relationship and extending between end supports 176, 178. The tensioning bands 177, 179 can be composed of the same material as the flexible member 170, or alternatively of a different material. The flexible member 170 can be formed with two seams so a tension band can be threaded through the seam in manufacture and welded to the membrane. When the flexible member 170 is spread by outer frame 110, the bands 177, 179 likewise stretch. Bands 177, 179, facilitate stretching of member 170 and the return of member 170 to its non-spread position when the frame 110 is moved to the un-expanded position. Bands 177, 179 also aid the sliding of the frame and insertion of the inner member 150. End support 176 is connected to the undersurface of frame portion 114 and end support 178 is connected to the undersurface of portion 130 by swaging or by other methods such as snap fit or ultrasonic staking, thereby connecting flexible member 170 to the outer frame 110.

The frame supports 176 and 178 each have a pair of tabs 176a, 176b which function as a stop for frame portion 114 and 130. That is, as shown in FIG. 11, movement of frame portion 112 away from frame portion 130 is limited by tabs 176a due to the abutment with wall 113a. Movement of frame portion 130 away from frame portion 112 is limited by tabs 176b abutting a wall of frame portion 130. These tabs prevent disassembly of the outer frame.

The outer frame 110 of access port 100 is preferably sufficiently rigid to retain flexible member 170 in a tensioned configuration. As frame 110 is expanded (spread), flexible member 170 is tensioned and stretched radially outwardly to retract tissue and/or to expand the passageway 174 extending through member 170. The outer frame 110 can be flexible in the plane of the patient's body surface to allow it to conform to the shape of the patient's body, presenting a lower profile to surgeons.

More specifically, with reference to FIGS. 1, 2, 4, frame portion or member 112 of outer frame 110 has a transverse end wall 121 with arms 127, 128 extending therefrom, preferably at substantially right angles thereto, although other angles are contemplated. Arms 127, 128 transition into arm sections 123, 125. The arms 123, 125 and 127, 128 are preferably integral with end wall 121, however, in alternative embodiments, they can be separate components attached to the opposing end regions of wall 121. As shown, arm sections 123, 125 have a reduced profile in relation to arms 127, 128. That is, the height or thickness of arm section 123 is less than the height or thickness of arm section 127. Similarly, the height or thickness or arm section 125 is less than the height or thickness of arm section 128. Arm sections 123, 125 can have a smaller width than arms 123, 125. The arm sections 123, 125 are shown as extending substantially parallel to one another with a substantially planar upper surface 140, 146, respectively. The upper surface 140 of arm section 123 has a plurality of projections 141 forming an engagement structure. Similarly, the upper surface 146 of arm section 125 has a plurality of projections 147 forming an engagement structure. The projections in the illustrated embodiment include a plurality of discs (or spheres) arranged in a plurality of rows. Other arrays and a different number of projections are also contemplated. Projecting surfaces other than spheres (domes) are also contemplated to achieve the engaging/locking function described below. The projections 141 and 147 of arm sections 123, 125 form an engagement structure to receive the engagement structure of the frame portion 130 as described in detail below.

Locking portion or member 114 of outer frame 110 has an end wall 116 and arms 118 and 119 extending therefrom. The arms can be integrally formed with end wall 116, or alternatively, composed of separate components connected to opposing ends of the wall 116. End 118a of arm 118 and end 119a of arm 119 angle upward (proximally) to form angled camming walls described below. The arms 118, 119 are preferably substantially perpendicular to the end wall 116, although they can be positioned at other angles. The locking portion 114 has a lip 111 (FIG. 2C) for securement of the locking portion 130. Locking portion 114 has a lip 118c (FIG. 5) which acts as a stop (as it contacts side wall 139b of tab 135) to prevent disassembly of the locking portion 114. A similar lip on the other side of the locking portion 114 similarly interacts with a sidewall of tab 137.

Frame portion 112 includes a finger indentation 121a formed in wall 121 which is dimensioned and configured to receive a user's finger(s). Finger indentation 121a includes edge 121b and open end 121c. Similarly, locking portion 114 includes a finger indentation 116a formed in wall 116 which is dimensioned and configured to receive a user's finger(s). Finger indentation 116a includes an edge 116b and an open end 116c. Edges 121b and 116b form an abutment for the user's finger(s) to facilitate sliding movement of the portion 112 and portion 114 as described below. Directional arrows can be provided within the indentations 121, 116 to direct movement of these components as described below. Also, locking/unlocking graphics can be provided in the outer frame 110. Note the edges 121b and 116b are oriented in the same direction.

Frame portion or member 130 of outer frame 110 includes wall 132 with arms 134, 136, extending therefrom, either integrally or formed of separate components attached thereto. Arms 134, 136 can be positioned substantially perpendicular to the wall 132, or alternatively positioned at different angles. The wall 132 extends transversely with respect to arms 134, 136, and transverse to the direction of movement of the frame portions 112, 130, thus forming a transverse bridge for connection of the two locking arms 134, 136. The frame portion 130 is interposed between the first portion 112 and the locking portion 114 such that a section of the frame portion 130 overlies arm sections 123, 125 of first portion 112 and the arms 118, 119 of locking portion 114 overlie arms 134, 136 of frame portion 130 as shown in FIG. 1. Arms 136 and 138 include a lip on a lower surface to receive frame portion 112 (see e.g. lip 136a of FIG. 6).

Arm 134 of frame portion 130 includes a locking tab 135 and arm 136 includes a locking tab 137. The locking tabs 135, 137 form pivoting locking arms for locking engagement with the first portion 112. That is, the first pivoting locking arm or tab 135 is positioned on a first side of the frame portion 130. The tab 135 can be formed integrally with the frame portion 130, e.g. similar to an integral tab formed for example by a cutout. Alternatively, the tab 135 can be a separate element attached to the frame portion 130. A second pivoting locking arm or tab 137 preferably identical to locking tab 135 is provided on the opposing side of frame portion 130 and functions in the same manner as locking tab 135, and can be integral with or a separate component of frame portion 130.

More specifically, the undersurface or distal surface of the locking tabs 135, 137 each includes engagement structure for engaging the engagement structure on the arms 123, 125 of frame portion 112. The locking tabs 135, 137 are preferably biased upwardly (proximally) so that in their normal position their engagement structure is out of engagement, or at least out of locking engagement, with the engagement structures on the respective arm sections 123, 125 as shown in the cross-sectional view of FIG. 5. The ends 118a and 119a of locking portion 114 have a ramped surface 118b to force the locking tabs 135, 137 downwardly toward arm sections 123, 125 to engage the engagement structures of the arm sections 123, 125 to lock the frame portions 112, 130 in a spread position as shown in the cross-sectional view of FIG. 11.

That is, the locking mechanism for frame 110 maintains frame portions 112, 130 in a select spread position by engagement of a first engagement structure on one arm 134 and a second engagement structure on the other arm 136 of frame portion 130. The locking member or locking portion 114 is selectively relatively slidable with respect to the second frame portion 130 in a direction along a longitudinal axis of the outer frame 110 to move the engagement structures on arms 134 and 136, e.g. locking tabs 135 and 137, in a direction transverse to the longitudinal axis of the outer frame 110 into locking engagement with the projections 141, 147 on arms 123, 125 of frame portion 112. In this manner, the first and second portions 112, 130 of the outer frame 110 are moved apart to a desired spread position to expand and stretch the flexible member 170 and then retained or locked in the select position by relative movement of the locking member 114 with respect to the second portion 130 which substantially simultaneously causes tabs 135, 137 to lockingly engage both arms 123, 125 of frame portion 112 due to their connection by transverse bridge 132 and due to the connection of ends 118a and 119a of locking portion 114 by wall 129 also forming a transverse bridge. Note the term relatively slidable includes one or both of the locking portion 114 and frame portion 130 moving relative to the other portion.

The undersurface of tab 135 includes a plurality of projecting surfaces 133. In a preferred embodiment, the projecting surfaces 133 are disc like members, e.g. domes or spheres, similar in configuration to projections 141, 147. In the illustrated embodiment they are arranged in three rows, two across, however other arrays and a different number of projections are also contemplated, as well as other configurations, e.g. domes or spheres (balls). Similarly, the undersurface of tab 137 includes a plurality of projecting surfaces 131. In a preferred embodiment, the projecting surfaces 131 are also dome or sphere (ball) like members. In the illustrated embodiment, they are arranged in three rows, two across, however other arrays are also contemplated. Projecting surfaces 131 are preferably configured and arranged in the same manner as projecting surfaces 133.

The pivoting tabs 135, 137 are preferably biased to a position away from the second portion 112 so in its normal position their respective projections 133, 131 do not engage (or at least do not lockingly engage) the projections 141, 147 of frame portion 112. That is, as shown in FIG. 5, the tabs 135, 137 are spring biased upwardly to a first non-engaged position. Tab 135 has an upper surface 139, for engagement by the angled camming surface 118b of end 118 of the locking portion 114, described below. Tab 137 likewise has an upper surface, for engagement by the angled camming surface of the end 119 of locking portion 114. Consequently, when the frame portion 130 and second portion 114 are relatively moved with respect to each other (either one moving toward the other or both moving toward each other), camming surface 118b of end 118 engages the upper surface 139 of tab 135, thereby forcing the tab 135 downwardly as viewed in FIG. 11 so that projecting surfaces 133 engage the projections 141 of arm section 123. The projecting surfaces 133 are dimensioned to fit within and move between the spaces 142 of the select projections 141. Likewise, when the locking portion 114 and second portion 130 are relatively moved with respect to each other (either one moving toward the other or both moving toward each other), the camming surface of end 119a of arm 119 engages the upper surface of tab 137, thereby forcing the tab 137 downwardly so that the projecting surfaces 131 engage the projections 147 of arm section 125. The projecting surfaces 131 move between the spaces of the select projections 147. This engagement of projections 141, 147 restricts movement of the first and second portions 112, 130. Thus, in use, once the desired spread position of the first portion 112 and second portion 130 is achieved to tension flexible member (e.g. membrane) 170 and retract tissue, locking member 114 and/or second portion 130, are slid toward each other to pivot arms (tabs) 135, 137 into engagement with the projecting surfaces 141, 147 on arm sections 123, 125 of frame portion 112, thereby clamping (securing) outer frame 110 in the select spread position.

Second portion 130 can include a finger indentation 130a with an end wall 130b and an open end 130c. The finger indentation 130a is oriented in an opposite direction of finger indentation 116a of locking portion 114 such that walls 116b, 130b face each other. This facilitates movement of the locking member 114 and/or the second portion 130 toward each other. Note in preferred embodiments, locking portion 114 moves toward frame portion 114 and 112 to perform its camming and locking function so as not to affect the tension on flexible member 170 during locking.

In the alternate embodiment of FIG. 2A, cushioning pads are provided to reduce irritation to the patient's skin. The access port 300 of FIG. 2A is identical to the access port 100 of FIG. 2, except for the cushioning pads. Therefore, for convenience, the identical parts of access port 300 have been labeled with reference numerals identical to those of FIG. 2 except they have been changed to the "300 series." Consequently, access port 300 has for example an outer frame 310, with first portion 312, second portion 330, and locking portion 314. Access port 300 also includes flexible member 370 secured at a proximal end to outer frame 310 and at a distal end to inner frame 350. Inner frame 350 has a lip 352, surrounding an opening 155, which together with passage 374 in member 370 and opening 317 in outer frame 310 enable passage of surgical instrumentation into the body cavity. Not all the corresponding parts between access port 300 and access port 100 have been labeled for clarity, and for brevity further discussion of identical components to access port 100 is not provided.

Turning now to the different feature of access port 300, the port 300 includes a first cushioning pad 390 and a second cushioning pad 392. The pads 390, 392 can be composed of material such as polyurethane foam, although other materials are also contemplated. An upper surface 390a of pad 390 is attached to an undersurface of portion 330 of outer frame 310 by thermal bonding. An upper surface 392a of pad 392 is attached to an undersurface of portion 312 of outer frame 310 by similar methods. The pads 390, 392 can be arcuate shaped to conform to the respective undersurface of portions 312, 330. In the embodiments where the flexible member is supported by a base, 375 similar to base 175 of FIGS. 1 and 2, the pads 390, 392 can be attached by thermal bonding to the undersurface of the end supports 376 (which are similar to end supports 176). In use of the port 300, when the port 300 is placed on the patient's skin, the pads 390, 392 contact the patient's skin rather than the frame portions 312, 330 or base 175.

The use of the access port will now be described in conjunction with the embodiment of FIG. 1, it being understood that the access port 300 of the embodiment of FIG. 2A would work in a similar fashion. The use of the access port will be described for thoracic surgery, it being understood that it can also be utilized in other surgical procedures to provide access to an internal region, e.g. an internal cavity, of the patient to enable insertion of surgical instrumentation therethrough.

Initially, an opening, or incision, is made in the patient's outer tissue wall of the thoracic body cavity by conventional means. The incision is made between adjacent ribs "R" (FIG. 8), extending along the intercostal space, and is relatively narrow and elongated.

For insertion through the incision, the inner member 150 is bent or reconfigured to reduce its transverse dimension for insertion through the patient's incision and into the body cavity. Note different sizes of access ports can also be used to accommodate different patients and/or incision lengths.

With inner (distal) member 150 inserted and then released, the access port 100 is in position such that the inner member 150 is positioned within the body cavity adjacent the inner portion of the incision, flexible member 170 extends through the incision to outside the patient's body, and upper (outer) frame 110 rests on the patient's skin. The outer frame 110 can now be expanded to tension and stretch the flexible member 170 due to the attachment of the flexible member 170 to the outer frame 110 to retract tissue adjacent the ribs R and to widen the passageway 174 through the flexible member 170. Note in this placement position, in the illustrated embodiment, the longitudinal axis of the frame 150 is substantially parallel to a long axis of the incision and the longitudinal axis of outer frame 110 is substantially transverse to the long axis of the incision, the longitudinal axis defining the longer dimension of the respective frame. Stated another way, the longer width dimension W of inner frame 150 and the shorter width dimension H of outer frame 110 are substantially parallel to a long axis of the incision.

In the initial position of access port 100 as shown in FIG. 8, flexible member 170 defines a funnel shape with frame 110 retaining proximal end 172 of flexible member 170 while distal end 171 of flexible member 170 defines a smaller diameter due to the engagement of distal end 171 with the smaller dimensioned lip 152 of inner frame 150. In this initial position, lip 152 is configured to seat a rib "R" of a patient therein to protect the rib "R," the intercostal nerve, and surrounding tissue. That is, lip 152 extends upwardly into the opening in tissue adjacent the ribs "R" (see FIG. 3). Additional cushioning (not shown) may be provided on lip 152 and/or an upper surface of frame 150 to provide further protection to ribs "R" and to surrounding tissue. Outward flexion of flexible member 170 expands the intercostal space, thus maximizing passageway 174 and giving access port 100 the maximum length. If the access port 300 is utilized, the cushioning material 390, 392 is in contact with the patient's skin to provide a less abrasive surface.

To spread the first and second sections 112 and 130 of frame 110 to stretch (radially tension) the flexible member 170 to retract tissue adjacent the ribs and incision and widen the incision passageway for passage of surgical instrumentation, the user can place his/her finger(s) of one hand in indentation 121a of portion 112 of outer frame 110 and place his/her finger(s) of the other hand in indentation 130a of portion 130. The frame portions 112 and 130 are then moved away from each other in the direction of the arrows on first portion 112 and second portion 130 (FIG. 9). Note the fingers of the user can abut the walls 121b, 130. Note that due to the connection of locking portion 114 and second portion 130 of outer frame 110, when second portion 114 is moved in the direction of the arrow, locking portion 114 is also moved together with the second portion 130 in that direction.

Note, as an alternative to utilizing the finger indentations, the user can otherwise grasp wall 121 of the first portion 112 and wall 132 of second portion 130 or wall 116 of locking portion 114 and spread them away from each other to expand the distance between end walls 113 and 115 to tension the flexible member 170.

Note the tissue is spread by actuation of the outer frame 110 transverse to the long axis of the incision. When the desired spread position, i.e. desired tissue retraction, is achieved, the user is now ready to lock (secure) the outer frame 110 in its selected spread position. To achieve this, the user can place one or more of his/her finger(s) of one hand in the indentation 130a of second portion 130 and one or more of his/her finger(s) in the indentation 116a of locking portion 114 and then squeeze them together in the direction of the arrows in indentation 116a and the direction of the arrow adjacent indentation 130a. Note the user's finger(s) can abut the respective walls 130b and 116b of indentations 130a, 116a, respectively. Such squeezing causes relative movement of second portion 130 and locking member 114, e.g. moves locking portion 114 in a direction toward first portion 112, to the position of FIG. 10. This movement causes the camming surface 118b of end 118a to engage the upper surface 139 of locking tab 135 to cam the locking tab 135 from the unlocked or unengaged position of FIG. 5 to the locking or engaged position of FIG. 11. Likewise, such movement causes the camming surface of end 119a to engage the upper surface of locking tab 137 to cam the locking tab 137 from the unlocked or unengaged position to the locking or engaged position. That is, prior to such movement, the projecting surfaces 133, 131 of locking tabs 135 and 137 are out of engagement, or at least out of locking engagement, with the projecting surfaces 141, 148 of arm sections 123, 125 of frame portion 112. Upon such movement, the projecting surfaces 133, 131 of locking tabs 135 and 137 are cammed into engagement with the projections 141, 147 of arm sections 123, 125, so the projecting surfaces 133, 131 are interposed between the spaces between projecting surfaces 141, 147 to limit slippage. This maintains the frame portions 112, 130 in a select spread (expanded) position, i.e. locks (or clamps) them against further movement during insertion of surgical instruments through access port 100.

With access port 100 secured in the desired expanded position, surgical instrumentation may be inserted through opening 117, passageway 174, and opening 155 to perform the surgical procedure within the body cavity. The low-profile configuration of access port 100, along the external surface of tissue, allows for greater access to the thoracic cavity "T" and for greater manipulation of instrumentation disposed through passageway 174.

Upon completion of the surgical procedure, second portion 130 and/or locking member 114 is relatively moved in the opposite direction (away from each other) toward their original position to release the camming surfaces from the upper surface of pivoting tabs 135, 137 to allow them to move to their unlocked non-engaged position, thereby allowing the frame portions 112, 130 to be moved toward each other toward their initial non-expanded (non-spread) position to untension flexible member 170. Next, the surgeon may grasp inner member 150 e.g., with a surgical tool, to fold or reconfigure it to reduce its transverse dimension to remove it from the thoracic cavity and through the incision.

As will be appreciated, access port 100 is easily inserted, manipulated, and removed from a patient's body. Further, the access port 100 is minimally intrusive, flexible to conform to a patient's anatomy, and provides good visibility into the thoracic cavity "T" (FIG. 3). Additionally, the low-profile configuration of access port 100 is particularly advantageous, for example, in the removal, or retrieval, of tissue specimens from within the body.

The flexible member 170 may be coated with a lubricant, or gel, to aid in the insertion and removal of surgical instrumentation and/or tissue specimens from access port 100.

Although described for use in thoracic procedures, it should also be understood that the access ports described herein can be used in other minimally invasive surgical procedures.

Persons skilled in the art will understand that the devices and methods specifically described herein and illustrated in the accompanying figures are non-limiting exemplary embodiments, and that the description, disclosure, and figures should be construed merely exemplary of particular embodiments. It is to be understood, therefore, that the present disclosure is not limited to the precise embodiments described, and that various other changes and modifications may be effected by one skilled in the art without departing from the scope or spirit of the disclosure. Additionally, it is envisioned that the elements and features illustrated or described in connection with one exemplary embodiment may be combined with the elements and features of another without departing from the scope of the present disclosure, and that such modifications and variations are also intended to be included within the scope of the present disclosure. Accordingly, the subject matter of the present disclosure is not to be limited by what has been particularly shown and described, except as indicated by the appended claims.

What is claimed is:

1. A method of accessing an internal portion of a patient comprising: providing an access assembly including: an outer frame positionable outside the patient and defining an opening therein, the outer frame including discrete first and second portions and a locking mechanism for locking the discrete first and second portions of the outer frame in one of a plurality of select expanded positions, at least one of the first and second other of the first and second portions to adjust the opening, the opening portions being movable with respect to the dimensioned to receive a surgical instrument therethrough;

the locking mechanism including a first engagement structure on the first portion selectively engageable with a second engagement structure on the second portion, the locking mechanism being repositionable between a locked position, wherein the first and second engagement structures are engaged, and an unlocked position, wherein the first and second engagement structures are disengaged, the locking mechanism being biased toward the unlocked position, and a slidable member movable to reposition the locking mechanism from the unlocked position to the locked position to retain the first and second portions in a selected expanded position;

wherein the second engagement structure comprises a first soft material and a second material on opposing sides of the opening,
wherein the first engagement structure includes a first substantially rigid projecting member having a first ramped surface and a first sharp tip embeddable within the first soft material;
wherein the first engagement structure includes a second substantially rigid projecting member having a second ramped surface and a second sharp tip embeddable within the second soft material;
wherein the slidable member comprises a first and a second collars positioned around and slidable relative to the first and second portions of the outer frame, the first collar is capable of contacting the first ramped surface to pivot the first sharp tip into the first soft material, and the second collar is capable of contacting the second ramped surface to pivot the second sharp tip into the second soft material;
an inner member positionable within the patient; and
a flexible member extending between the inner member and the outer frame and operatively associated with the outer frame, the flexible member having a passageway to receive the surgical instrument therethrough, wherein movement of the first and second discrete portions of the outer frame adjusts tension on the flexible member to retract tissue;
inserting the inner member through an opening in tissue into a body of the patient with the flexible member extending proximally through the opening in tissue;
moving one of the first and second portions of the outer frame in relation to the other of the first and second portions into a selected unlocked spread position to enlarge the opening in tissue and the passageway through the flexible member; and
subsequently moving the locking mechanism to move the first and second engagement structures into a locking position to lock the first and second portions in the selected spread position.

2. The method of claim 1, further comprising introducing the surgical instrument through the opening in the outer frame and the passageway in the flexible member.

3. The method according to claim 1, wherein moving the locking mechanism includes moving the locking member with respect to the second portion.

4. The method of claim 1, wherein moving the locking mechanism to move the first and second engagement structures into the locking position includes camming the first and second engagement structures into engagement with first and second surfaces of the outer frame.

5. The method of claim 1, wherein moving at least one of the first and second portions includes sliding the first portion in a direction away from the second portion.

6. The method of claim 1, wherein moving the locking mechanism includes sliding the locking member toward the first portion.

7. The method of claim 1, further comprising inserting a specimen retrieval apparatus through the passageway in the flexible member.

8. The method of claim 1, wherein inserting the inner member includes folding the inner member for insertion through the tissue opening.

9. The method of claim 1, wherein inserting the inner member includes inserting the inner member into a thoracic cavity of the patient.

10. A method of accessing a thoracic cavity of a patient for performing minimally invasive thoracic surgery comprising:
providing an access assembly including:
an outer frame defining an opening therein, the outer frame including discrete first and second portions relatively movable to adjust the opening and a locking mechanism for locking the discrete first and second portions of the outer frame in one of a plurality of select expanded positions,
the opening dimensioned to receive a surgical instrument therethrough to access the thoracic cavity,
the locking mechanism including a first engagement structure on the first portion selectively engageable with a second engagement structure on the second portion, the locking mechanism being repositionable between a locked position, wherein the first and second engagement structures are engaged, and an unlocked position, wherein the first and second engagement structures are disengaged, the locking mechanism being biased toward the unlocked position, and a slidable member movable to reposition the locking mechanism from the unlocked position to the locked position to retain the first and second portions in a selected expanded position;
wherein the second engagement structure comprises a first soft material and a second material on opposing sides of the opening,
wherein the first engagement structure includes a first substantially rigid projecting member having a first ramped surface and a first sharp tip embeddable within the first soft material;
wherein the first engagement structure includes a second substantially rigid projecting member having a second ramped surface and a second sharp tip embeddable within the second soft material;
wherein the slidable member comprises a first and a second collars positioned around and slidable relative to the first and second portions of the outer frame, the first collar is capable of contacting the first ramped surface to pivot the first sharp tip into the first soft material, and the second collar is capable of contacting the second ramped surface to pivot the second sham tip into the second soft material;
a flexible member extending distally from the outer frame, the flexible member having a passageway dimensioned to receive the surgical instrument therethrough to access the thoracic cavity;
moving at least one of the first and second portions of the outer flame to a selected unlocked spread position to enlarge the opening in tissue and the passageway through the flexible member; and
moving the locking member to move the first and second engagement structures into a locking position to lock the first and second portions of the outer flame in the selected spread position.

11. The method of claim 10, wherein the access assembly includes an inner member, the flexible member extending proximally from the inner member, and the method further includes inserting the inner member through the opening in tissue and intercostal space into the thoracic cavity of the patient with the flexible member extending proximally through the opening in tissue.

12. The method of claim 10, further comprising introducing the surgical instrument through the passageway into the thoracic cavity.

13. The method of claim 10, wherein moving the locking mechanism to move the first and second engagement structures into the locking position includes camming the first and second engagement structures into engagement with first and second surfaces on the first portion.

14. The method of claim 13, wherein moving at least one of the first and second portions includes sliding the first portion in a direction away from the second portion.

15. The method of claim 14, wherein moving the locking mechanism includes sliding the second portion toward the locking mechanism.

16. The method of claim 10, further comprising inserting a specimen retrieval apparatus through the passageway and into the thoracic cavity.

17. The method of claim 11, wherein inserting the inner member includes folding the inner member for insertion through the tissue opening.

18. The method of claim 1, wherein providing the access assembly includes providing the outer frame such that at least one of the first and second portions defines an internal space configured and dimensioned to slidably receive the other of the first and second portions to facilitate relative movement between the first and second portions.

19. The method of claim 10, wherein providing the access assembly includes providing the locking mechanism as a discrete component of the access assembly separate from the first and second portions of the outer frame.

20. The method of claim 10, wherein providing the access assembly includes providing the outer frame such that at least one of the first and second portions defines an internal space configured and dimensioned to slidably receive the other of the first and second portions to facilitate relative movement between the first and second portions.

21. The method of claim 10, wherein providing the access assembly includes providing the locking mechanism as a discrete component of the access assembly separate from the first and second portions of the outer frame.

* * * * *